Figure 1:
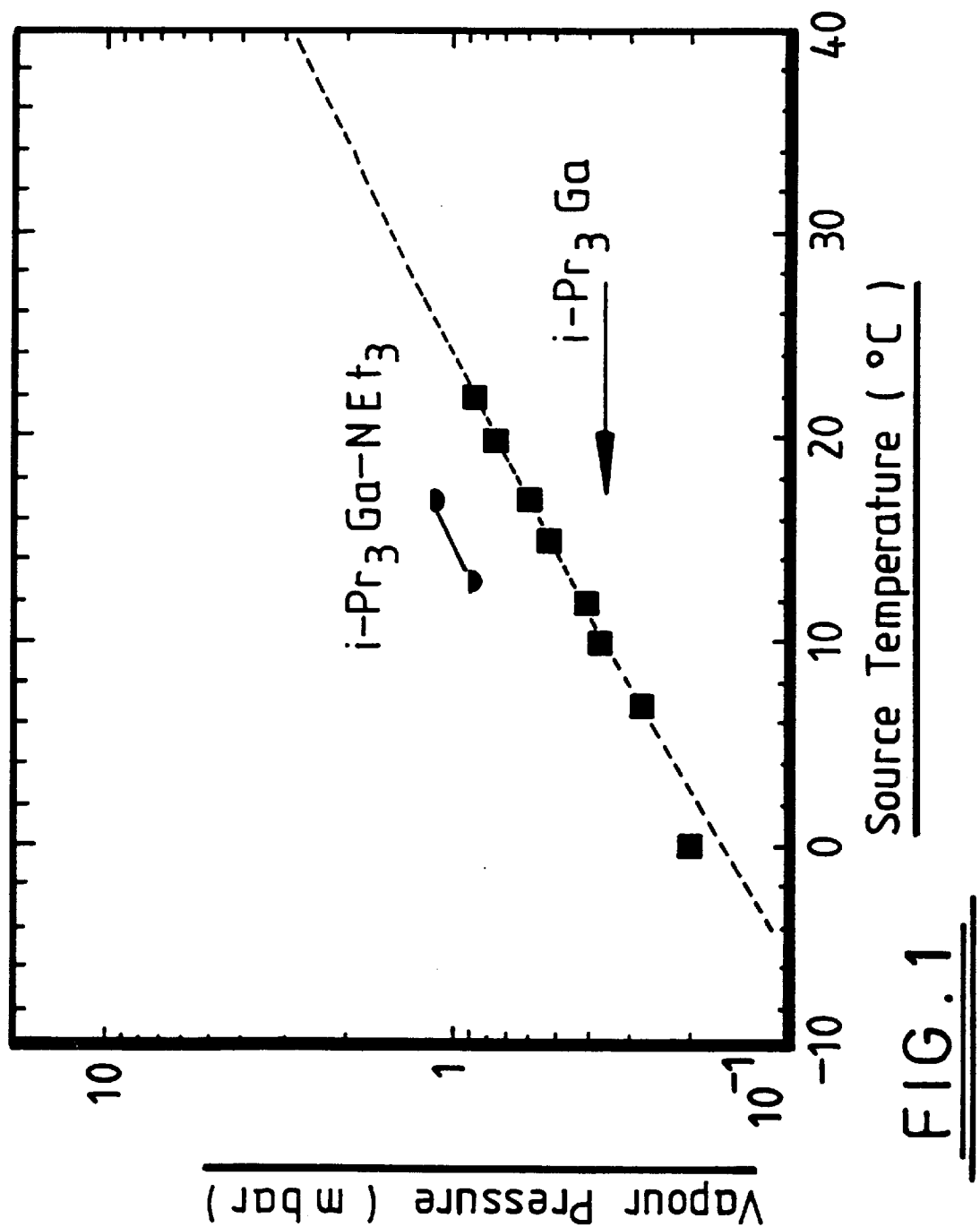

United States Patent [19]
Jones et al.

[11] Patent Number: 5,886,203
[45] Date of Patent: Mar. 23, 1999

[54] METALORGANIC COMPOUNDS

[75] Inventors: Anthony Copeland Jones, Prescot; Simon Andrew Rushworth, Wirral; Trevor Martin, Malvern; Timothy John Whittaker, Malvern; Richard William Freer, Malvern, all of United Kingdom

[73] Assignee: Secretary of State For Defence Acting Through His Defence Evaluation & Research Agency, Malvern, United Kingdom

[21] Appl. No.: 793,809

[22] PCT Filed: Sep. 4, 1995

[86] PCT No.: PCT/GB95/02087

§ 371 Date: Jul. 14, 1997

§ 102(e) Date: Jul. 14, 1997

[87] PCT Pub. No.: WO96/07660

PCT Pub. Date: Mar. 14, 1996

[30] Foreign Application Priority Data

Apr. 28, 1995 [GB] United Kingdom ............... 9508702
Sep. 2, 1995 [GB] United Kingdom ............... 9417707

[51] Int. Cl.⁶ ................................................. C07F 7/22
[52] U.S. Cl. ................... 556/96; 556/1; 556/9; 556/13; 556/27; 556/64; 556/81; 556/101; 556/102; 556/170; 556/400; 546/2; 546/12; 544/225; 540/310
[58] Field of Search ............... 540/310; 556/129, 556/128, 1, 9, 13, 27, 64, 81, 96, 101, 102, 170, 400; 544/225; 546/2, 12

[56] References Cited

U.S. PATENT DOCUMENTS 4,812,586  3/1989  Mullin et al. ............... 556/129

OTHER PUBLICATIONS

*Inorganic Chemistry*, vol. 7, No. 6, 1968, Henrickson, C.H. et al., "Lewis Acidity of Alanes. Interactions of Trimethylalane with Amines, Ethers, and Phosphines, " pp. 1047–1051.

*Journal of Inorganic and Nuclear Chemistry*, vol. 26, 1964, Stevens, L.G. et al., "Organogalium Compounds III. The Heat of Dissociation of Triethyl and Trivinylgallium Addition Compounds," pp. 97–102.

*Journal of the Chemical Society, Dalton Transactions*, 1988, Foster, D.F. et al., Synthesis and Thermal Properties of Adducts of Trimethylindium with Nitrogen–Containing Lewis Bases, pp. 7–11

*Chemische Berichte*, vol. 122, 1989, Neumüller, B., "Synthese und Eigenschaften von $iPr_2InCl$, $iPrInCl_2$ und $(iPr_2InNHtBu)_2$," pp. 2283–2287

*Chemical Abstracts*, vol. 114, No. 21, May, 1991, Hoffman, G.G. et al., "Synthesis, Properties, and some reactions of Isopropylgallium Haldies and Tris(isopropyl)gallane," pp. 838.

Primary Examiner—James O. Wilson
Attorney, Agent, or Firm—Howell & Haferkamp, L.C.

[57] ABSTRACT

A process is provided for the production of metalorganic compounds by reacting a Grignard reagent with a Group II, Group III or Group V metal halide in a tertiary alkyl amine solvent to form a metalorganic adduct, isolating the adduct and dissociating the adduct to leave the metalorganic compound.

9 Claims, 3 Drawing Sheets

METALORGANIC COMPOUNDS

This application is the U.S. National Stage of International application Ser. No. PCT/GB95/02087, filed Sept. 4, 1995, which derives its priority from Great Britain Patent applications Ser. No. 9508702.9, filed Apr. 28, 1995 and 9417707.8, filed Sept. 2, 1994.

DESCRIPTION

This invention concerns metalorganic compounds, especially metalorganic compounds used in the growth of semi-conductor layers by vapour phase epitaxial techniques, such as by chemical beam epitaxy, MOVPE, or ALE.

Metalorganic precursors used in semiconductor growth are generally synthesised by reacting a Grignard reagent such as an alkyl magnesium halide RMgX or an alkyl lithium compound with a metal halide. The formation of the Grignard reagent and its subsequent reaction with a metal halide to form the precursor are carried out in an oxygen containing solvent, typically an ether. Subsequent purification processes are then performed to remove the oxygen containing ether solvent and other impurities from the metalorganic precursor.

Unfortunately residual trace amounts of ether can result in oxygen contamination of semi-conductor structures grown using the above prepared precursors. Consequently, there is a deleterious effect on the properties of the semiconductor structures.

The existence of metalorganic amine adducts, has been disclosed in for example the reports of Henrickson C. H. et al (Inorganic Chemistry, vol. 7, no 6 1968 pages 1047–1051) and Stevens, L. G. et al (Journal of Inorganic and Nuclear Chemistry, vol. 26, 1964, pages 97 –102).

An object of this invention is to provide a method of preparing metalorganic compounds that avoids the above-mentioned disadvantages.

According to this invention there is provided a process for preparing a metalorganic compound by reacting a Grignard reagent with the metal halide, characterised in that said reaction is carried out in an amine solvent.

The Grignard reagent for use in the process of the invention is preferably prepared in an amine solvent, especially the amine to be used in preparing the metalorganic compound.

The amine is preferably a tertiary amine such as, for example, a tertiary alkyl amine or a tertiary heterocyclic amine. Amines for use in the invention are preferably liquid at room temperature, typically 18° to 20° C. Tertiary alkyl amines for use in the invention preferably have the formula

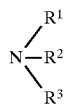

wherein $R^1$, $R^2$ and $R^3$ are alkyl groups having from 1 to 4 carbon atoms and wherein $R^1$, $R^2$, and $R^3$ may be the same or two of $R^1$, $R^2$ and $R^3$ may be the same. Preferred alkyl amines for use in the invention are triethylamine and dimethylethylamine.

Suitable heterocylic amines for use in the invention may include pyridine, 2H-pyrrole, pyrimidine, pyrazine, pyridazine, 1,3,5-triazine and hexahydrotriazine.

The Grignard reagent may be prepared in any suitable way, typically by reaction of magnesium with an alkyl halide, wherein the alkyl group is that required for the metalorganic compound.

Metalorganic compounds that may be prepared in accordance with the invention include alkyl compounds of Group II, Group III and Group V metals. Examples of such compounds include dialkyl zinc, dialkyl cadmium, trialkyl aluminium, trialkyl gallium, trialkyl indium, trialkyl phosphorus, trialkyl arsenic and trialkyl antimony.

It is believed that the process of the present invention results in an adduct of the metalorganic compound with the amine. The formation of this adduct permits the removal of volatile metallic and nonmetallic microimpurities from the metalorganic compound. Impurities may be readily removed from the adduct by distillation. The adduct may be split by removal of the amine, such as by heating, to provide the metalorganic compound alone for some purposes, such as a precursor for MOVPE or CBE. Alternatively the adduct itself may be used as a precursor for the deposition of, for example Group III-V or II-VI layers, such as gallium arsenide, aluminium gallium arsenide and zinc selenide, by MOVPE, CBE and other vapour phase epitaxy techniques.

A preferred process according to the invention includes the following steps:

1. Synthesis of RMgX in $NR_3$ solvent;
2. Suspension of $MCl_3$ in pentane;
3. Addition of RMgX to $MCl_3$ in $NR_3$/pentane;
4. Removal of volatiles and isolation of $MR_3(NR_3)$ by distillation;
5. Removal of volatile impurities from $MR_3(NR_3)$;
6. Isolation of the adduct or thermal dissociation of $MR_3(NR_3)$ and removal by fractional distillation of the $NR_3$ ligand.

The invention will now be further described by means of the following examples. Each reaction described below was carried out in an atmosphere of dry/oxygen-free dinitrogen using reagents which had been dried and deoxygenated by standard purification methods.

EXAMPLE 1

This example demonstrates the production of triisopropylgallium using triethylamine as solvent.

A solution of iso-propyl magnesium bromide, i-PrMgBr, in triethylamine was prepared by the dropwise addition of iso-propyl bromide, i-PrBr (280 g, 2.3 mol) to a stirred suspension of magnesium metal turnings (60 g, 2.5 mol) in triethylamine, $NEt_3$ (1000 cm$^3$). This resulted in a vigorous exothermic reaction. It was found that this reaction could be more easily initiated by the addition of a crystal of iodine. After complete addition of the i-PrBr, the reaction mixture was stirred at ambient temperature for 4 hours.

A solution of gallium trichloride, $GaCl_3$ (125 g, 0.7 mol) in pentane (500 cm$^3$) was then added slowly with stirring to the solution of i-PrMgBr in $NEt_3$. This led to an exothermic reaction. After complete addition of the $GaCl_3$-pentane solution, the reaction mixture was stirred for 4 hours at room temperature to ensure complete reaction.

After removal of volatiles by distillation in vacuo, the crude product was isolated by vacuum distillation (100° C.) into a receiver cooled in liquid nitrogen (ca-196° C.). Volatile impurities were removed from the crude product by distillation invacuo (25°–50° C.) and the pure liquid product was obtained by vacuum distillation (80° C.) into a cooled receiver (ca-106° C.).

The metalorganic product was identified using proton NMR spectroscopy as a triethylamine adduct of triisopropylgallium, i-$Pr_3Ga(NEt_3)$0.6·

The proton NMR data are summarised below:

| (ppm) | (Assignment) |
|---|---|
| 0.8 (triplet, 5.4H) | NCH$_2$C$\underline{H}_3$ |
| 1.0 (multiplet, 3H) | GaC$\underline{H}$(CH$_3$)$_2$ |
| 1.4 (doublet, 18H) | GaCH(C$\underline{H}_3$)$_2$ |
| 2.4 (quartet, 3.6H) | NC$\underline{H}_2$CH$_3$ |

The i-Pr$_3$Ga-NEt$_3$ adduct was further analysed for trace metal impurities using inductively coupled plasma emission spectroscopy (ICP-ES). The only impurities detected were silicon (0.03 ppm w.r.t. Ga) and. zinc (0.2ppm w.r.t. Ga).

Yield i-Pr$_3$Ga(NEt$_3$)$_{0.6}$=49.4 g.

The vapour pressure of the iPr$_3$Ga adduct was found to be 0.9 mBar ar 13° C.

The tri-isopropyl gallium prepared in the above way was used to grow a layer of AlGaAs on a gallium arsenide substrate by chemical beam epitaxy under the following conditions:

| | |
|---|---|
| Substrate temperature | 540° C. |
| AlGaAs growth rate | 1/hr |
| Group V precursor - | thermally cracked arsine |
| Group III precursors - | tri-isopropyl gallium triethylamine adduct plus AlH$_3$—NMe$_2$Et |

An AlGaAs layer (aluminium composition of 18%) grown in this manner demonstrated oxygen levels of less than 4×10$^{16}$ cm$^{-3}$ (as measured by secondary ion mass spectrometry, SIMS). This layer is superior to an AlGaAs layer (aluminium composition of 25%) grown using triisopropylgallium synthesised in a conventional manner (i.e. using an ether solvent), and AlH$_3$(NMe$_2$Et), in which much higher oxygen levels of 9×10$^{16}$ cm$^{-3}$ were detected by SIMS. The AlGaAs layer grown using the triisopropyl gallium-triethylamine adduct was comparable in oxygen content (<4×10$^{16}$cm$^{-3}$) with the best layers thus far obtained using triethylgallium and AlH$_3$(NMe$_2$Et) under identical CBE growth conditions.

Figure 2:
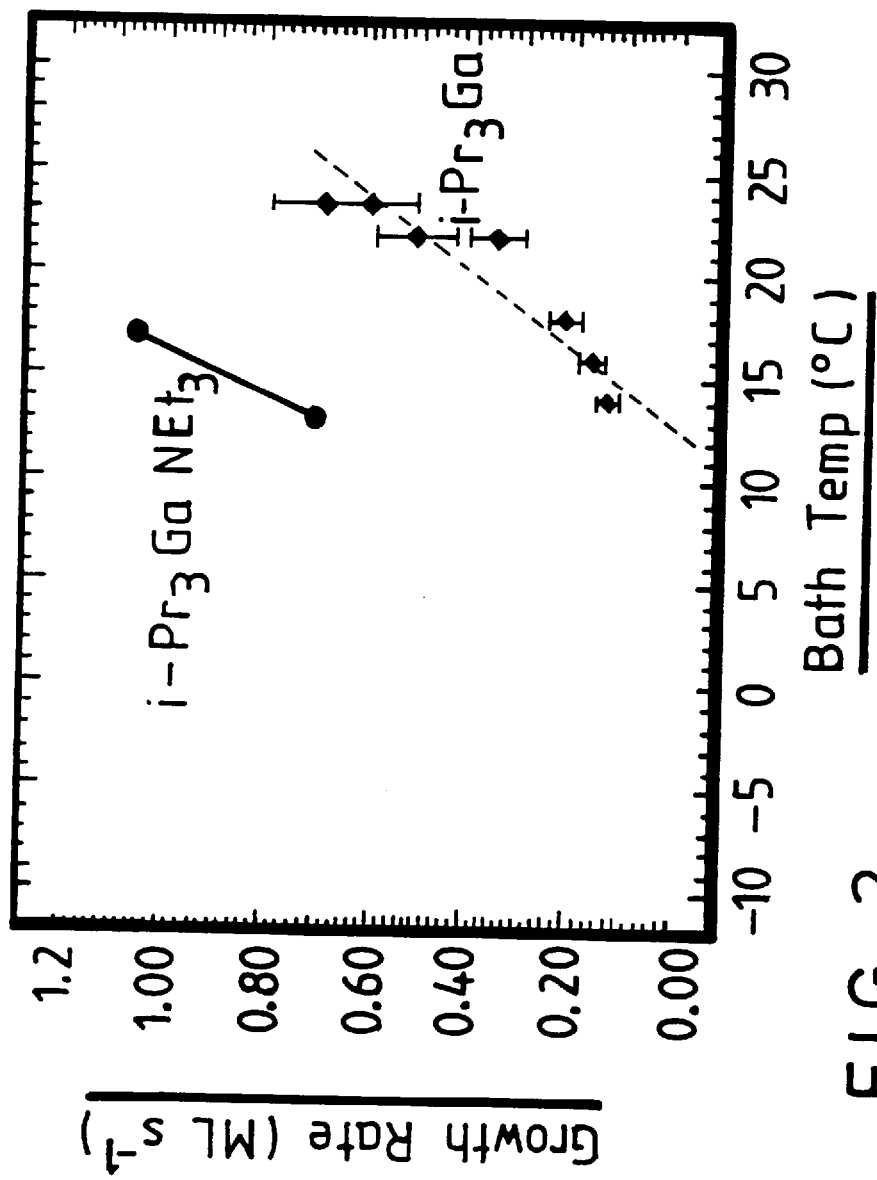
Figure 3:
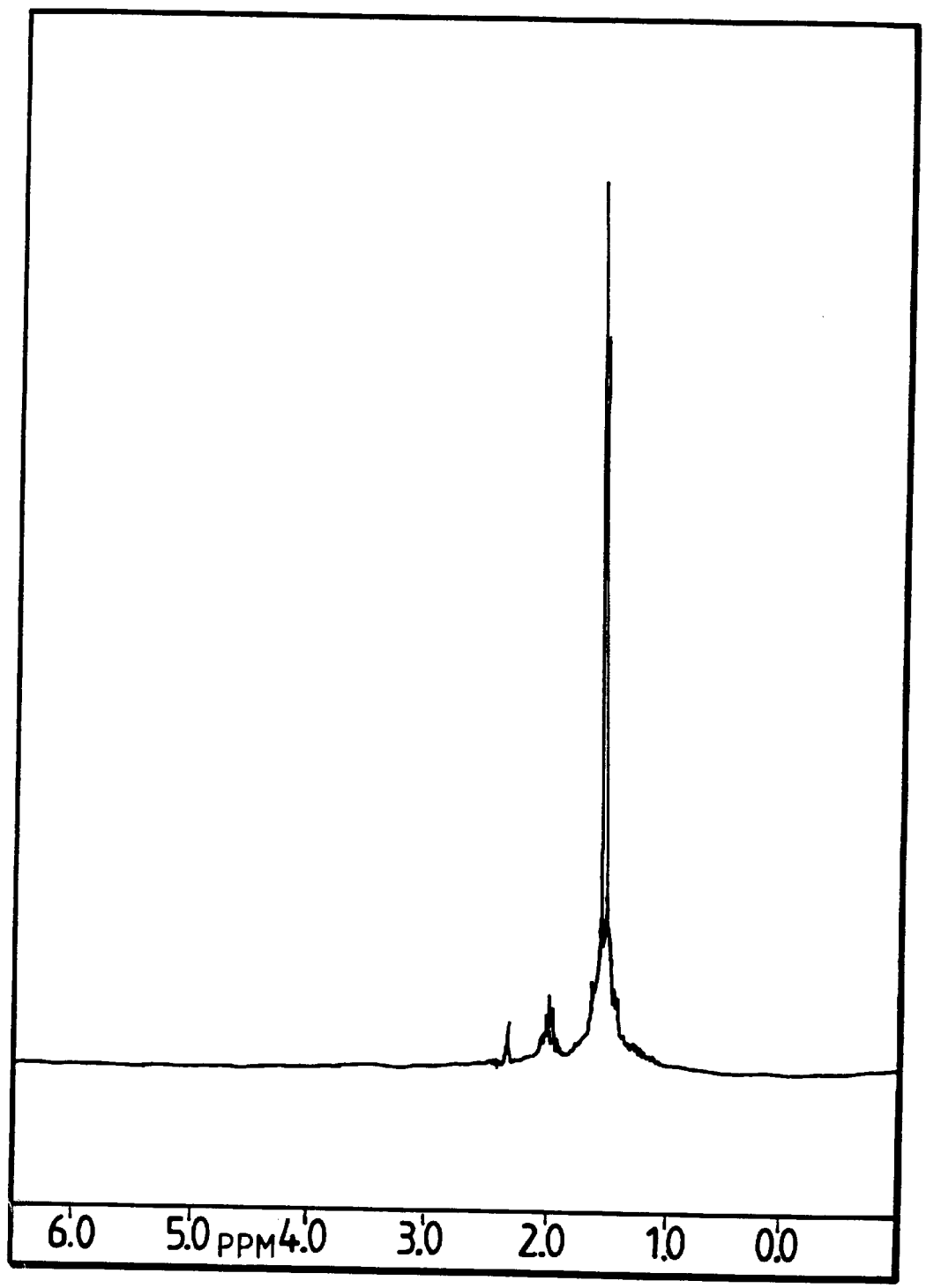

FIGS. 1 and 2 respectively of the accompanying drawings show comparison of vapour pressures and growth rates of the tri-isopropyl gallium adduct prepared according to this Example and tri-isopropyl gallium prepared in the conventional way. As can be seen the adduct has both higher vapour pressures and growth rates which are advantageous for chemical vapour deposition processes.

EXAMPLE 2

This demonstrates the production of triisopropylgallium using dimethylethylamine as solvent.

A solution of iso-propylmagnesium bromide, i-PrMgBr, in dimethylethylamine was prepared by the dropwise addition of iso-propylbromide, i-PrBr (166 g, 1.4 mol) to a stirred suspension of Mg metal turnings (48 g, 2.0 mol) in dimethylethylamine, NMe$_2$Et (500 cm$^3$). This resulted in a vigorous exothermic reaction which could be more easily initiated by the addition of a small quantity of iodine. After complete addition of the i-PrBr the reaction mixture was stirred at room temperature for 4 hours.

A solution of GaCl$_3$ (69 g, 0.4 mol) in pentane (260 cm$^3$) was then added slowly, with stirring, to the solution of i-PrMgBr in NMe$_2$Et. This led to a vigorous exothermic reaction. After complete addition of the GaCl$_3$-pentane solution, the reaction mixture was stirred for 4 hours at room temperature to ensure complete reaction.

After removal of volatiles by atmospheric pressure distillation (60° C.), the crude product was isolated by vacuum distillation (100° C.) into a cooled receiver (ca-196° C.). Volatile impurities were removed from the crude products in vacuo, and the pure liquid product was obtained by reduced pressure distillation (70° C.) into a receiver.

The metalorganic product was identified using proton NMR spectroscopy as the dimethylethylamine adduct of triisopropylgallium, i-Pr$_3$Ga(NMe$_2$Et). The proton NMR data are summarised below:

| (ppm) | (Assignment) |
|---|---|
| 0.6 (triplet, 3H) | NCH$_2$C$\underline{H}_3$ |
| 0.9 (multiplet, 3H) | GaC$\underline{H}$(CH$_3$)$_2$ |
| 1.4 (doublet, 18H) | GaCH(C$\underline{H}_3$)$_2$ |
| 1.9 (singlet, 6H) | NC$\underline{H}_3$ |
| 2.4 (quartet, 2H) | NC$\underline{H}_2$CH$_3$ |

The i-Pr$_3$Ga-NMe$_2$Et adduct was further analysed for trace metal impurities using ICP-ES. The only impurities detected were silicon (0.2 ppm w.r.t Ga) and Zinc (4.6 ppm w.r.t Ga).

Yield i-Pr$_3$Ga(NMe$_2$Et)=58.5 g

EXAMPLE 3

This example demonstrates the production of triisopropylindium using triethylamine as solvent.

A solution of i-PrMgBr in NEt$_3$ was prepared by the dropwise addition of i-PrBr (72 g, 0.6mol) in NEt$_3$ (200 cm$^3$). This led to a vigorous exothermic reaction. After complete addition of the i-PrBr the reaction mixture was stirred at room temperature for 4 hours.

The solution of i-PrMgBr in NEt$_3$ was added dropwise, with stirring, to a suspension of indium trichloride, InCl$_3$ (35 g, 0.2 mol) in NEt$_3$(200 cm$^3$). This led to an exothermic reaction. After complete addition of the i-PrMgBr/NEt$_3$ solution, the reaction mixture was boiled under reflux for 2 hours.

After removal of volatiles by distillation in vacuo, the crude product was obtained by vacuum distillation (100° C.) into a cooled receiver (ca-196° C). Volatile impurities were removed from the crude product by distillation in vacuo and the pure liquid product was obtained by vacuum distillation (70° C.) into a cooled receiver (ca-196° C.).

The metalorganic product was identified using proton NMR spectroscopy as a triethylamine adduct of triisopropylindium, i-Pr$_3$In(NEt$_3$). The proton NMR data are summarised below:

| (ppm) | (Assignment) |
|---|---|
| 0.8 (triplet, 9H) | NCH$_2$C$\underline{H}_3$ |
| 1.1 (multiplet, 3H) | InC$\underline{H}$(CH$_3$)$_2$ |
| 1.6 (doublet, 18H) | InCH(C$\underline{H}_3$)$_2$ |
| 2.4 (quartet, 6H) | NC$\underline{H}_2$CH$_3$ |

The i-Pr$_3$In-NEt$_3$ adduct was further analysed for trace metal impurities using ICP-ES. The only impurities detected were silicon (0.04 ppm w.r.t In) and zinc (3.8 ppm w.r.t In).

Yield i-Pr$_3$In(NEt$_3$)=8 g.

EXAMPLE 4

This example demonstrates the production of triisopropylindium using dimethylethylamine as solvent.

A solution of i-PrMgBr in NMe$_2$Et was prepared by the dropwise addition of i-PrBr (192 g, 1.6 mol) to a stirred suspension of Mg metal turnings (56 g, 2.3 mol) in NMe$_2$Et (400cm$^3$).

This resulted in a vigorous exothermic reaction. After complete addition of the i-PrBr the reaction mixture was stirred for 4 hours at room temperature.

The solution of i-PrMgBr in NMe$_2$Et was added dropwise, with stirring, to a suspension of InCl$_3$ (72 g, 0.3 mol) in pentane. This resulted in an exothermic reaction. After complete addition of the i-PrMgBr/NMe$_2$Et solution, the reaction mixture was boiled under reflux for 2 hours.

After removal of volatiles by atmospheric pressure distillation, (60° C.), the crude product was obtained by reduced pressure distillation (85°–90° C.) into a receiver. Volatile impurities were removed from the crude product by vacuum distillation (25° C.).

The pure liquid product was obtained by vacuum distillation (85°–90° C.) into a receiver cooled to approx. −196° C.

The straw yellow liquid was identified using proton NMR spectroscopy as the dimethylethylamine adduct of tri-isopropyl indium, iPr$_3$In(NMe$_2$Et). The proton NMR data are summarised below:

| (ppm) | (Assignment) |
|---|---|
| 0.8 (triplet, 3H) | NCH$_2$C$\underline{H}_3$ |
| 1.0 (multiplet, 3H) | InC$\underline{H}$(CH$_3$)$_2$ |
| 1.5 (doublet, 18H) | InCH(C$\underline{H}_3$)$_2$ |
| 2.0 (singlet, 6H) | NC$\underline{H}_3$ |
| 2.3 (quartet, 2H) | NC$\underline{H}_2$CH$_3$ |

The i-Pr$_3$In-NMe$_2$Et adduct was further analysed for trace metal impurities using ICP-EAS. The only impurities detected were silicon (<1 ppm) w.r.t In), and Zn(0.12 w.r.t In).

Yield i-Pr$_3$In(NMe$_2$Et)=81.7 g.

We claim:

1. A process for preparing a Group II, Group III or Group V metalorganic compound comprising reacting in a tertiary alkyl amine solvent a Grignard reagent with a Group II, Group III or Group V metal halide to form a metalorganic adduct, isolating the adduct and dissociating the adduct to leave the metalorganic compound.

2. A process as claimed in claim 1, wherein the amine is liquid at room temperature.

3. A process as claimed in claim 1, wherein the amine has the formula:

wherein R$^1$, R$^2$ and R$^3$ are alkyl groups having from 1 to 4 carbon atoms and wherein R$^1$, R$^2$ and R$^3$ are the same or two of R$^1$, R$^2$ and R$^3$ are the same.

4. A process as claimed in claim 3, wherein the amine is selected from the group consisting of triethylamine and dimethylethylamine.

5. A process as claimed in claim 1, wherein the metalorganic compound is selected from the group consisting of trialkyl aluminium, trialkyl gallium, trialkyl indium, trialkyl phosphorous, trialkyl arsenic and trialkyl antimony.

6. A process as claimed in claim 5, wherein the alkyl groups of the metalorganic compound comprise isopropyl groups.

7. A process as claimed in claim 5, wherein the alkyl groups of the metalorganic compounds include one or more isopropyl groups.

8. A process for preparing a Group II, Group III or Group V metalorganic compound comprising the steps of preparing a Grignard reagent in a tertiary alkyl amine solvent; reacting the Grignard reagent with a Group II, Group III or Group V metal halide in the tertiary alkyl amine solvent to form a metalorganic adduct; isolating the metalorganic adduct formed; and dissociating the metalorganic adduct to leave the metalorganic compound.

9. A process as claimed in claim 8, wherein the Grignard reagent is prepared by reacting magnesium with an alkyl halide and wherein the metalorganic compound contains an alkyl group supplied by the metal halide.

* * * * *

UNITED STATES PATENT AND TRADEMARK OFFICE
CERTIFICATE OF CORRECTION

PATENT NO. : 5,886,203
DATED : March 23, 1999
INVENTOR(S) : Jones, et al

It is certified that error appears in the above-indentified patent and that said Letters Patent is hereby corrected as shown below:

On the title page: Item [30]

under "Foreign Application Priority Date", the priority date of patent application [GB] United Kingdom....9417707, should be shown as Sep. 2, 1994, rather than Sep. 2, 1995.

Signed and Sealed this

Twelfth Day of October, 1999

Attest:

Q. TODD DICKINSON

*Attesting Officer*     *Acting Commissioner of Patents and Trademarks*